(12) United States Patent
Geertsema

(10) Patent No.: US 6,439,233 B1
(45) Date of Patent: Aug. 27, 2002

(54) TRACHEAL STOMA VALVE

(75) Inventor: Albert Geertsema, Groningen (NL)

(73) Assignee: ADEVA Medical Gesellschaft für Entwicklung und Vertrieb von Medizinischen Implantat-Artikeln mbH, Lubeck (DE)

( * ) Notice: Subject to any disclaimer, the term of this patent is extended or adjusted under 35 U.S.C. 154(b) by 0 days.

(21) Appl. No.: 09/494,930

(22) Filed: Feb. 1, 2000

(30) Foreign Application Priority Data

Feb. 1, 1999 (EP) ............................................. 99101965

(51) Int. Cl.⁷ .............................................. A61M 16/00
(52) U.S. Cl. ............................ 128/207.16; 128/204.19; 251/12; 251/298
(58) Field of Search ................... 128/207.15, 207.16, 128/200.24, 204.18, 204.19, 205.24, 207.14; 251/12, 298, 42, 301; 137/599.11, 625, 625.44, 625.45

(56) References Cited

U.S. PATENT DOCUMENTS

| | | |
|---|---|---|
| 3,827,440 A | 8/1974 | Birch et al. |
| 4,582,058 A * | 4/1986 | Depel et al. ............ 128/207.17 |
| 5,123,922 A * | 6/1992 | Berg ............................. 623/9 |
| 5,259,378 A * | 11/1993 | Huchon et al. ......... 128/207.16 |
| 5,765,560 A * | 6/1998 | Verkerke et al. ....... 128/201.16 |
| 6,189,534 B1 * | 2/2001 | Zowtiak et al. ........ 128/207.16 |

FOREIGN PATENT DOCUMENTS

| | | |
|---|---|---|
| DE | 2253 496 | 5/1973 |
| EP | 0 221 973 B1 | 5/1987 |
| EP | 0 617 630 B1 | 10/1994 |
| GB | 2 164 424 A | 3/1986 |

* cited by examiner

*Primary Examiner*—Glenn K. Dawson
(74) *Attorney, Agent, or Firm*—Akin, Gump, Strauss, Hauer & Feld, L.L.P.

(57) ABSTRACT

A tracheal stoma valve with a valve housing (2) has a pivotable valve flap (3), which is pivotable upon inhalation with an air stream of predeterminable strength into a position sealing off the open lumen (4) of the valve housing (2), and upon exhalation with an air stream of predeterminable strength is pivotable into a position at least partially clearing the open lumen (4) again. Moreover, a bypass valve (5) is provided, through which breathing air can be inhaled when the valve flap (3) is located in the closed position. The two mentioned switching points of the valve flap (3), between the sealing position and the position at least partially clearing the open lumen (4) of the valve housing (2), are pre-adjustable.

6 Claims, 2 Drawing Sheets

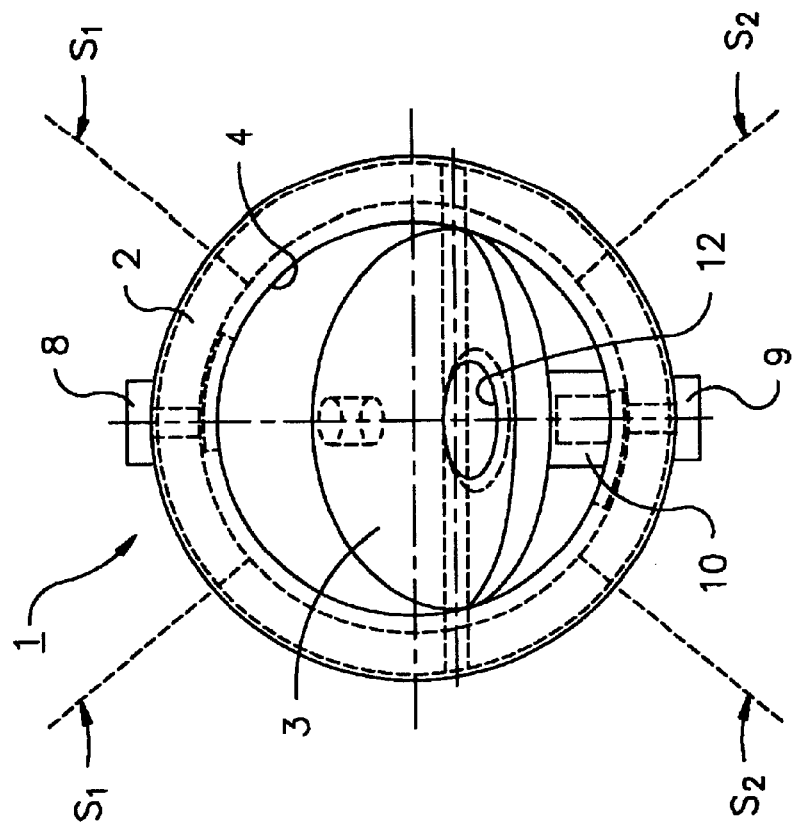
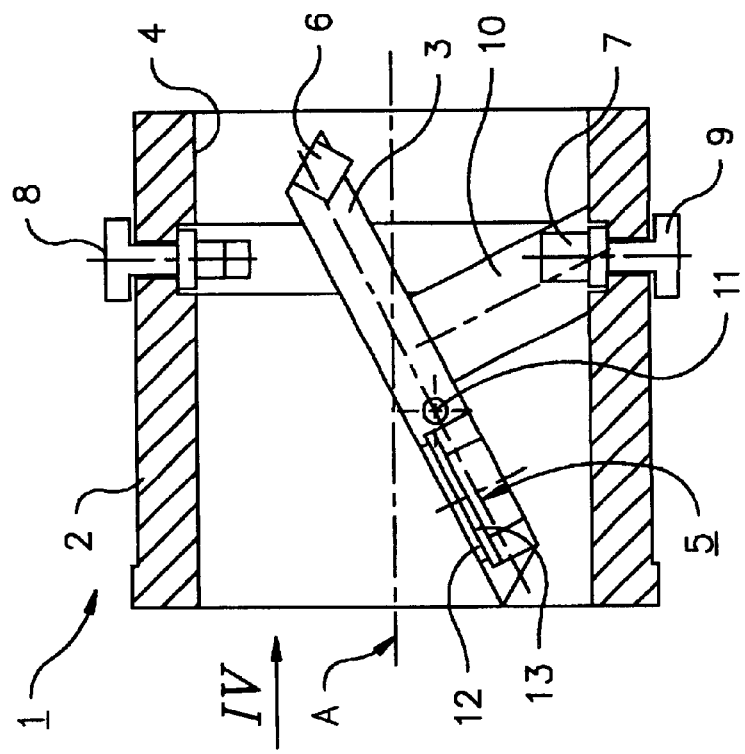

TRACHEAL STOMA VALVE

BACKGROUND OF THE INVENTION

The present invention relates to a tracheal stoma valve or vent. Such valves are known, for example, from European patents EP-B-0 221 973 and EP-B-0 617 630.

In the tracheal stoma valve mentioned in the latter publication, the valve has a valve closing element, which closes the valve in response to an air displacement. This is occasioned by the patient to be able to direct the air through a shunt valve between the trachea and the esophagus, in order to maintain a certain speaking capacity. In addition, the valve mentioned has a so-called blow-off valve element which, during response to a particular pressure, opens on the tracheal side of the valve. Consequently, when coughing, one needs to take care that the blow-off valve element opens and the air and sputum can be expressed from the stoma. This function is important, since otherwise severe complications can occur if, for example, the secretion (sputum) reaches the lobe of the lung where it can lead to severe infections.

With the known valve the blow-off valve element has an opening which is closable by the first mentioned valve closing element. In this way, the air can be so redirected that it can be guided through the mentioned shunt valve.

If the patient wishes to speak, a portion of the air stream must thus serve during exhalation for activating the mentioned valve closing element, so that this can be brought into its closed position. In addition, the patient must activate the valve closing element in the speaking mode once per breath, so that after each inhalation, he/she can bring the valve closing element back into the closed position, in order to be able to direct the stream of air by the shunt valve.

Even though the known valve has considerable advantages in comparison to older valve constructions, activating the valve closing element each time during speaking mode is felt by the patient to be uncomfortable.

SUMMARY OF THE INVENTION

An object of the present invention therefore consists in increasing the comfort of the patient while safety remains constant. This object is accomplished by a tracheal stoma valve according to the present invention. Further refinements and embodiments are described below and in the dependent claims.

Accordingly, it is provided that the tracheal stoma valve has a valve housing in which a valve flap is pivotably mounted. This is pivotable, upon inhalation with an air stream of a predeterminable strength, into a position sealing off the open lumen of the valve housing and, upon exhalation with an air stream of predeterminable strength, is pivotable into a position at least partially clearing the open lumen again. Moreover, it has a bypass valve element, through which respiratory air can be inhaled when the valve flap is in the closed position, whereby the two first switching points of the valve flap between the sealing position and the position at least partially clearing the open lumen of the valve housing are pre-adjustable.

The valve of the invention thus closes with its valve flap in an intensified inhalation operation, whereas the valve according to the cited EP-B-0 671 630 closes with an intensified exhalation. In contrast, the valve of the invention must be opened again by an intensified exhalation pressure, which, however, is conducive to the safety aspect if during coughing, etc. an overpressure is built up in the trachea which must be reduced through the valve. Here, the valve flap of the tracheal stoma valve of the invention to this extent also assumes the function of the blow-off valve element in the valve of the previously mentioned publication.

By an intensified inhalation the patient switches the tracheal stoma valve into speaking mode. With the subsequent exhalation no air escapes from the valve through the stoma, but instead is guided through the shunt or through the appropriate shunt valve, after which it is available for forming sounds and articulation. If the patient wishes to continue to keep the valve in speaking mode, he/she can once again inhale through the bypass valve element without the valve flap having to be pivoted even on short term and for a short time into the position at least partially clearing the open lumen of the valve housing. After successful inhalation has taken place, air is then directed again past the stoma by the shunt valve.

In contrast to the valves according to the prior art, it is not necessary here with each breath to activate the valve closing element mentioned there in order to activate further inhalations. The bypass valve element, which for switching (namely for closing upon beginning to speak) needs only the motion of a relatively small and light valve disk, ensures this.

According to a particularly preferred embodiment, it is provided that at least two permanent magnets are arranged on the valve flap, such that the one permanent magnet forms, with a first metallic sliding valve arranged in the valve housing, a magnetic closure in the sealing position of the valve flap, and the second permanent magnet forms, with a second sliding valve arranged in the valve housing, a magnetic closure in the position of the valve flap at least partially clearing the open lumen of the valve housing. This embodiment offers a very comfortable possibility of adjusting the switching points of the valve flap already mentioned, in that the holding force of the magnetic closures can be increased or decreased by activation of the respective sliding valve, since the contact between the permanent magnet and metallic sliding valve, and consequently the appropriate holding force, is greater or smaller, depending on the position of the sliding valve, as already known per se from the prior art.

An especially preferred embodiment provides that the bypass valve element is constructed as a recoil valve integrated into the valve flap. The recoil valve must open independently during the inhalation process and correspondingly close during the exhalation process. The recoil valve can here be constructed as automatically closing, so that the patient practically needs to use hardly any force or hardly any partial air stream at all, in order to close the bypass valve during the exhalation process, to keep the entire tracheal stoma valve in speaking mode.

Particularly preferred is an embodiment in which the valve flap is eccentrically suspended in the valve housing, by which it is to be understood that the center of gravity of the valve flap lies below the longitudinal axis of the valve housing. In this way, it can be achieved that the surface of the valve flap effectively exposed to the respective air stream upon the respective inhalation or exhalation process can be most effectively actuated, in order to be able to generate the torque (around the center of gravity) required for the pivoting motion.

A catch or limit stop can be formed on the valve flap for restricting the pivoting motion, in order to keep the valve flap constantly in a defined position. If the valve flap has such a catch, it is particularly preferred to provide that the already-mentioned second permanent magnet with the construction of magnetic closures, which is provided for a magnetic closure in the position of the valve flap at least partially clearing the open lumen of the valve housing, is arranged at the end of the catch. The first permanent magnet, which corresponds with the other position of the valve flap, can then be embedded on a face edge of the valve flap.

BRIEF DESCRIPTION OF THE SEVERAL VIEWS OF DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings:

FIG. 3 is a view similar to FIG. 1, showing the valve with the valve flap in a position in which the lumen is partially cleared; and FIG. 4 is a view of the valve in the direction of the arrow IV in FIG. 3.

In the following description the same reference numerals are used for respectively similar elements.

DETAILED DESCRIPTION OF THE INVENTION

Figure 1:
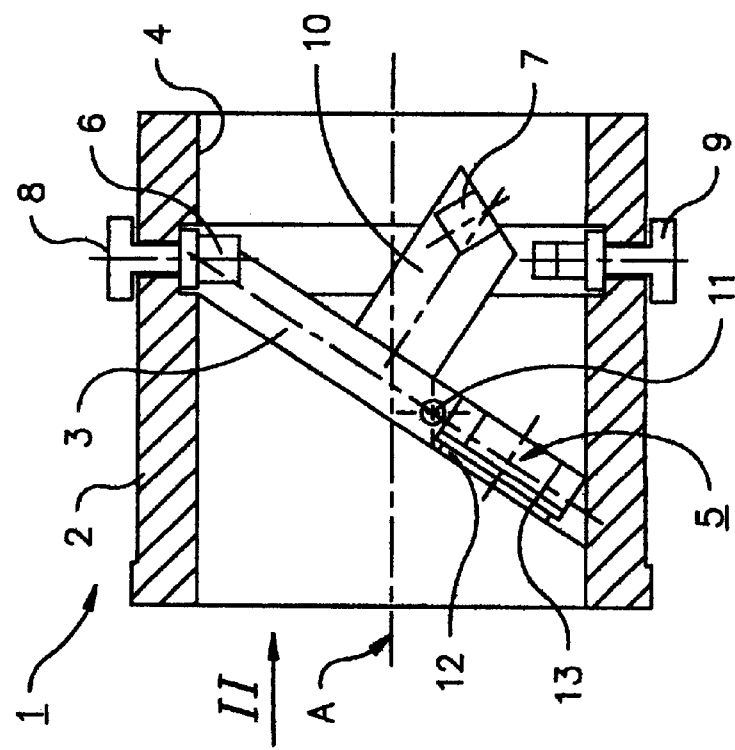
FIG. 1 is a section view of the tracheal stoma valve with the valve flap in the position sealing off the open lumen of the valve.

FIG. 1 shows the section view of the tracheal stoma valve 1. The tracheal stoma valve has a valve housing 2, which is here represented as a cylindrical tube. The valve housing 2 has an open lumen 4, through which air from the outside (to the right in FIG. 1) can flow into a trachea-side cannula piece (to the left in FIG. 1).

In the interior of the valve housing 2, a valve flap 3 is mounted, and indeed about an eccentrically positioned center of gravity 11. This thus lies below the longitudinal axis A of the valve housing 2. A catch 10 is formed on the valve flap 3, which restricts a pivoting motion from the position in accordance with FIG. 1 to a position in accordance with FIG. 3.

In the valve housing 2, a first metallic sliding valve 8 is arranged, which can be driven in a pivoting range $S_1$ (FIG. 2) on the valve housing 2. The metallic sliding valve 8, together with a permanent magnet 6, which is arranged at the end of the valve flap 3, forms a magnetic closure, whose holding force depends on the position of the magnetic sliding valve 8.

Figure 2:
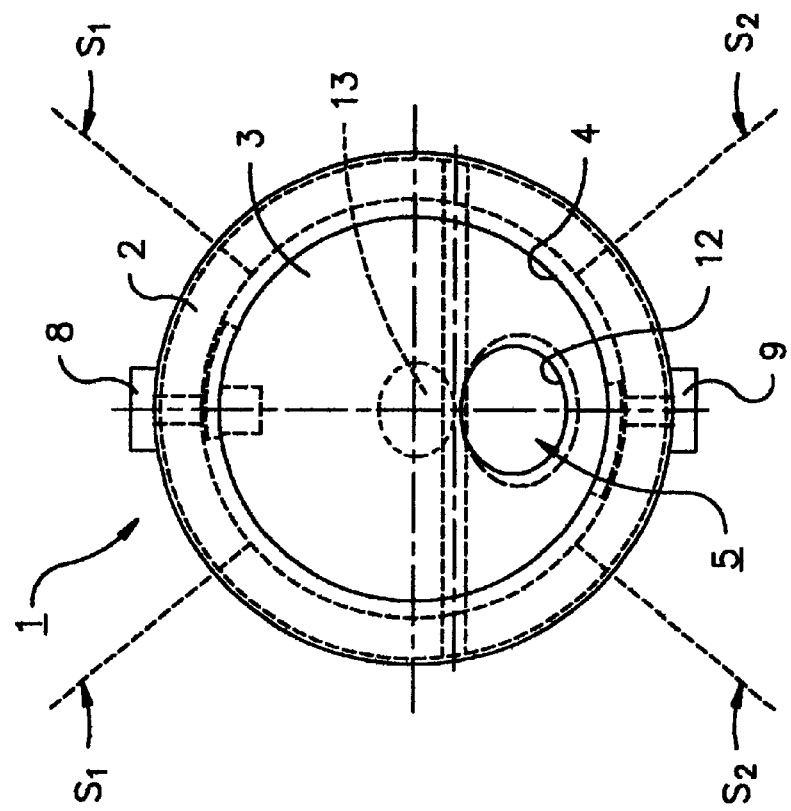
FIG. 2 is a view of the valve in the direction of the arrow II in FIG. 1.

Also arranged in the valve housing 2 is a correspondingly constructed second metallic sliding valve 9, which is correspondingly drivable in a pivoting range $S_2$ (FIG. 2). The second sliding valve 9, together with a permanent magnet 7, which is arranged on the end of the catch 10, forms a second magnetic closure, whose holding force correspondingly depends on the position of the sliding valve 9 in relation to the permanent magnet 7.

Depending on the switching position of the valve flap 3, one or the other magnetic closure is active. In the position represented in FIG. 1, in which the valve flap 3 seals off the open lumen 4 of the valve 1, the magnetic closure is active, due to the first permanent magnet 6 on the end of valve flap 3 and the first sliding valve 8, i.e., it holds the valve flap 3 in the represented position until a force exceeding the holding force engages the valve flap 3 in the form of an air stream.

Starting from the position of the valve flap 3 in FIG. 1, this is then the case when, through an intensified exhalation, a force exceeding the holding force of the first magnetic closure 6, 8 acts in order to pivot the valve flap 3 into the position according to FIG. 3. For this purpose, a strong air stream flows from left to right in FIG. 1, so that the valve flap 3 assumes the position in FIG. 3. While FIG. 1 represents the speaking mode of the tracheal stoma valve 1, the normal breathing mode is represented in FIG. 3.

A bypass valve 5 is integrated into the valve flap 3, which here is formed as a recoil valve with an opening 12 and a valve flap 13. If the tracheal stoma valve 1 is in normal respiratory mode, the bypass valve 5 practically exercises no function. Air is inhaled and exhaled by the patient through the partial lumen of the entire lumen 4 of the valve housing 2, cleared by the valve flap 3 (FIG. 4).

If the patient now wishes to switch the valve into the speaking mode, as represented in FIG. 1, he/she inhales somewhat more strongly than in normal breathing mode, so that then the holding force of the magnetic closure 7, 9 is no longer sufficient to hold the valve flap 3 in the position represented in FIG. 3. The valve flap 3 pivots instead into the position in accordance with FIG. 1, where it is held by the magnetic closure 6, 8. The normal breathing function is executed in this position of the valve flap 3 by the bypass valve 5, where the small valve flap 13 clears the valve opening 12 upon inhalation. The bypass valve 5 thus basically assumes its function in the speaking mode of the tracheal stoma valve 1. Once the tracheal stoma valve 1 is switched into speaking mode (FIG. 1), the patient practically no longer needs a partial air stream per breath to bring the tracheal stoma valve 1 into the speaking mode in which it is now already found, whereby the comfort of the patient upon speaking is considerably increased.

If, after speaking, the patient now wishes to convert the valve 1 again to the normal respiratory mode (FIG. 3), he/she exhales somewhat more strongly than in normal breathing mode, whereby the holding force of the magnetic closure 6, 8 is no longer sufficient to hold the valve flap 3 in the position in accordance with FIG. 1. This instead pivots back into the position in accordance with FIG. 3.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

I claim:

1. A tracheal stoma valve comprising a valve housing (2) having an open lumen (4) in which a valve flap (3) is pivotably mounted, the valve flap (3) being pivotable upon inhalation with a stream of air of a predeterminable strength into a position sealing off the open lumen (4) and the valve flap (3) being pivotable upon exhalation with a stream of air of predeterminable strength into a position at least partially clearing the open lumen (4) again, and a bypass valve (5) through which respiratory air can be inhaled when the valve flap (3) is found in the closed position, wherein the valve flap (3) has two switching points which are pre-adjustable between the position sealing off the open lumen (4) and the position at least partially clearing the open lumen (4).

2. The tracheal stoma valve according to claim 1, wherein at least two permanent magnets (6, 7) are arranged on the valve flap (3), such that one permanent magnet (6), with a first metallic sliding valve (8) arranged in the valve housing (2), forms a magnetic closure in the sealing off position of the valve flap (3), and a second permanent magnet (7), with a second sliding valve (9) arranged in the valve housing (2), forms a magnetic closure in the position of the valve flap (3) at least partially clearing the open lumen (4).

3. The tracheal stoma valve according to claim 1, wherein the bypass valve (5) is constructed as a recoil valve (12, 13) integrated into the valve flap (3).

4. The tracheal stoma valve according to claim 3, wherein the second permanent magnet (7) is arranged on the end of the catch (10).

5. The tracheal stoma valve according to claim 2, wherein a catch (10) for restricting the pivoting motion is formed on the valve flap (3).

6. The tracheal stoma valve according to claim 1, wherein the valve flap (3) is eccentrically suspended in the valve housing (2), such that the center of gravity (11) of the valve flap (3) lies below the longitudinal axis (A) of the valve housing (2).

* * * * *